(12) United States Patent
Kuwahara et al.

(10) Patent No.: US 8,911,422 B2
(45) Date of Patent: Dec. 16, 2014

(54) MICRO-NEEDLE DEVICE

(75) Inventors: Tetsuji Kuwahara, Tsukuba (JP); Seiji Tokumoto, Tsukuba (JP); Kazuya Machida, Tsukuba (JP)

(73) Assignee: Hisamitsu Pharmaceutical Co., Inc., Tosu-Shi, Saga (JP)

( * ) Notice: Subject to any disclaimer, the term of this patent is extended or adjusted under 35 U.S.C. 154(b) by 0 days.

(21) Appl. No.: 13/579,737

(22) PCT Filed: Feb. 24, 2011

(86) PCT No.: PCT/JP2011/054159
§ 371 (c)(1),
(2), (4) Date: Sep. 5, 2012

(87) PCT Pub. No.: WO2011/105496
PCT Pub. Date: Sep. 1, 2011

(65) Prior Publication Data
US 2012/0330250 A1    Dec. 27, 2012

(30) Foreign Application Priority Data
Feb. 24, 2010    (JP) ............... P2010-038718

(51) Int. Cl.
*A61M 31/00* (2006.01)
*A61M 37/00* (2006.01)
(52) U.S. Cl.
CPC ... *A61M 37/0015* (2013.01); *A61M 2037/0038* (2013.01); *A61M 2037/0046* (2013.01)
USPC ............... 604/500; 604/20; 604/22; 604/48; 604/264; 604/272; 604/501; 604/505

(58) Field of Classification Search
USPC ............... 604/118, 264, 265, 272, 20, 22, 48, 604/500, 501, 505
See application file for complete search history.

(56) References Cited

U.S. PATENT DOCUMENTS 7,537,795 B2 * 5/2009 Cormier et al. ............... 427/2.28
7,914,813 B2   3/2011 Adachi et al.
(Continued)

FOREIGN PATENT DOCUMENTS

JP    2004-510535 A    4/2004
JP    2005-533625 A    11/2005
(Continued)

OTHER PUBLICATIONS

International Preliminary Report on Patentability for International Patent Application No. PCT/JP2011/054159; mailed on Sep. 27, 2012.

(Continued)

*Primary Examiner* — Quynh-Nhu H Vu
*Assistant Examiner* — Larry R Wilson
(74) *Attorney, Agent, or Firm* — Nath, Goldberg & Meyer; Joshua B. Goldberg; Scott H. Blackman (57) ABSTRACT

An object of the present invention is to efficiently inject a drug (physiologically active substance). Therefore, a micro-needle device 1 comprises a base plate 2 and a micro-needle 3 installed on the base plate 2. A coating agent containing the physiologically active substance is coated at least at a part of the micro-needle 3, and a coating range thereof is 100 to 230 µm including the top of the micro-needle 3. A load due to the energy of 0.2 to 0.7 J/cm² is applied to the micro-needle device 1 which is in contact with the skin.

1 Claim, 7 Drawing Sheets

(56) References Cited

U.S. PATENT DOCUMENTS

| | | |
|---|---|---|
| 2002/0123675 A1* | 9/2002 | Trautman et al. ............ 600/309 |
| 2005/0251088 A1* | 11/2005 | Kwon ............................ 604/60 |
| 2005/0261631 A1 | 11/2005 | Clarke et al. |
| 2007/0250018 A1 | 10/2007 | Adachi et al. |
| 2008/0009811 A1 | 1/2008 | Cantor |
| 2008/0114298 A1 | 5/2008 | Cantor et al. |
| 2008/0183144 A1 | 7/2008 | Trautman et al. |
| 2009/0030365 A1 | 1/2009 | Tokumoto et al. |
| 2009/0099502 A1 | 4/2009 | Tokumoto et al. |
| 2010/0030100 A1 | 2/2010 | Tokumoto et al. |
| 2010/0221314 A1 | 9/2010 | Matsudo et al. |
| 2010/0280457 A1 | 11/2010 | Tokumoto et al. |

FOREIGN PATENT DOCUMENTS

| | | | |
|---|---|---|---|
| JP | 2006-341089 A | 12/2006 | |
| JP | 2007-037626 A | 2/2007 | |
| JP | 2007-260351 A | 10/2007 | |
| JP | 2011506023 A | 3/2011 | |
| WO | 2005/044333 A2 | 5/2005 | |
| WO | 2006/075689 A1 | 7/2006 | |
| WO | 2006/075716 A1 | 7/2006 | |
| WO | 2006/080508 A1 | 8/2006 | |
| WO | 2006/121110 A1 | 11/2006 | |
| WO | 2008/091602 A2 | 7/2008 | |
| WO | 2009/051147 A1 | 4/2009 | |
| WO | 2009/081122 A1 | 7/2009 | |

OTHER PUBLICATIONS

International Search Report for Japanese Patent Application No. PCT/JP2011/054159; mailed on Mar. 29, 2011.

* cited by examiner

MICRO-NEEDLE DEVICE

This is a National Phase Application filed under 35 U.S.C. §371 as a national stage of International Application No. PCT/JP2011/054159, filed on Feb. 24, 2011, claiming the benefit from Japanese Patent Application No. 2010-038718, filed on Feb. 24, 2010, the content of each of which is hereby incorporated by reference in its entirety.

TECHNICAL FIELD

The present invention relates to a micro-needle device for injecting through the skin a physiologically active substance which is provided on a base plate with a plurality of micro-needles capable of puncturing the skin.

BACKGROUND ART

There is conventionally known a micro-needle device as a device for improving percutaneous absorption of a drug. For example, Patent Literature 1 given below has disclosed a micro-needle device which is provided with a plurality of micro-needles which is in the shape of a tapered circular cone.

A method for injecting a drug coated on a micro-needle device includes, for example, a method for manually pushing and a method for using an auxiliary device, etc. With regard to the auxiliary device, for example, Patent Literature 2 given below has disclosed an applicator which gives an impact of at least 0.05 Joule per cm$^2$ to the micro-needle device within 10 milliseconds, thereby allowing the device to impact with the stratum corneum.

CITATION LIST

Patent Literature

Patent Literature 1: Japanese Translation of International Application No. 2005-533625
Patent Literature 2: Japanese Translation of International Application No. 2004-510535

SUMMARY OF INVENTION

Technical Problem

There is, however, a possibility that conventional methods may fail in efficiently injecting a drug in some cases. For example, such a case is found that a drug cannot be injected at a desirable dosage by using the device or adopting the method described in Patent Literatures 1 and 2 given above. Therefore, an object of the present invention is to provide a micro-needle device which is capable of efficiently injecting a drug (physiologically active substance).

Solution to Problem

The micro-needle device of the present invention is a micro-needle device comprises with a base plate and a micro-needle installed on the base plate in which a coating agent that contains a physiologically active substance is coated at least at a part of the micro-needle and a coating range of the coating agent is 100 to 230 μm in height including the top of the micro-needle, and a load due to the energy of 0.2 to 0.7 J/cm$^2$ is applied to the micro-needle device which is in contact with the skin.

The present inventor, et al., have conducted an earnest examination to solve the above problem and found that in a relationship between a coating range of a micro-needle and availability of a physiologically active substance, the greater the coating range, the lower the tendency of availability, but by adjusting the load applied to a micro-needle device, compensation can be made for the lower availability. According to the above-described invention, a coating agent including a physiologically active substance is coated in a range of 100 to 230 μm in height including the top of the micro-needle and a load (stress) from the energy of 0.2 to 0.7 J/cm$^2$ is applied to the micro-needle device, thus making it possible to efficiently inject the drug (physiologically active substance).

In the micro-needle device of the present invention, a load of the force of 1.0 to 10 kg may be applied to the micro-needle device in contact with the skin.

The present inventor, et al., also have conducted an earnest examination to solve the above problem and found that a load is applied twice or more to the micro-needle device in contact with the skin, thereby injecting a coated physiologically active substance efficiently. That is, in the micro-needle device of the present invention, a load may be applied at least twice to the micro-needle device in contact with the skin.

Advantageous Effects of Invention

According to the above-described micro-needle device, it is possible to inject a drug (physiologically active substance) efficiently.

BRIEF DESCRIPTION OF DRAWINGS

FIG. 3 (a) to (c) cover drawings which show one example of coating micro-needles.

DESCRIPTION OF EMBODIMENTS

Hereinafter, a detailed description will be given of the embodiments of the present invention by referring to attached drawings. In describing the drawings, the same or equivalent constituents are given the same reference signs to omit overlapping description.

Figure 1:
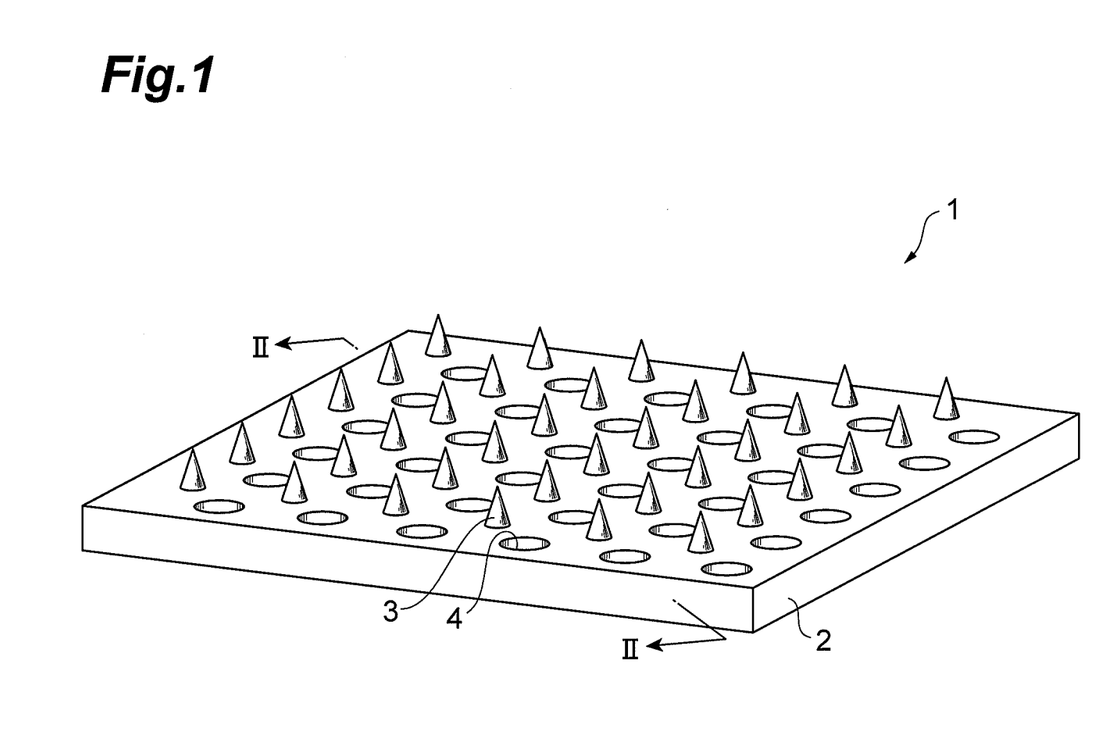
FIG. 1 is a perspective view which shows one example of a micro-needle device related to an embodiment.
Figure 2:
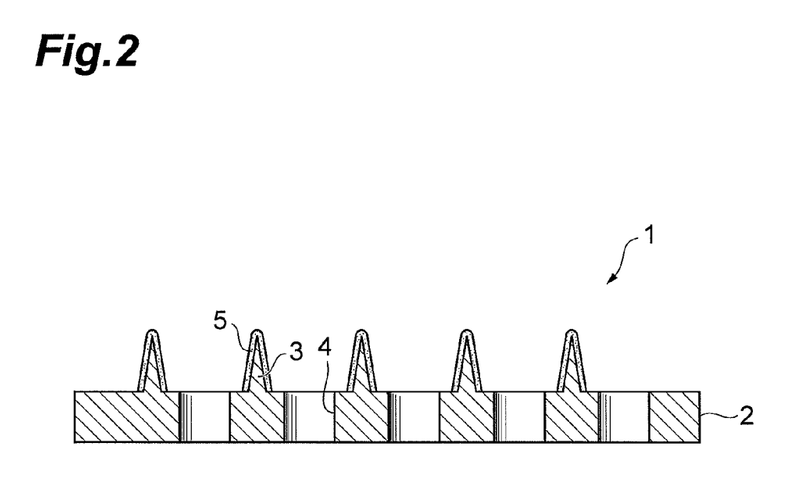
FIG. 2 is a sectional view taken along the line of II to II in FIG. 1.

FIG. 1 is a perspective view which shows one example of the micro-needle device related to an embodiment. FIG. 2 is a sectional view taken along the line of II to II in FIG. 1.

As shown in FIG. 1, the micro-needle device 1 comprises a micro-needle base plate 2 and a plurality of micro-needles 3 which are arranged two-dimensionally on the micro-needle base plate 2 and capable of puncturing the skin.

The micro-needle base plate 2 is a base for supporting the micro-needles 3. A plurality of through holes 4 are formed on the micro-needle base plate 2 so as to be arranged two-dimensionally. The micro-needles 3 and the through holes 4 are arranged alternately in a diagonal direction of the micro-needle base plate 2. The through holes 4 make it possible to inject a physiologically active substance from a back face of the micro-needle base plate 2 (the face on which no micro-needles 3 are installed). As a matter of course, there may be used a base plate which is free of these through holes.

The micro-needle base plate 2 is 0.5 cm$^2$ to 10 cm$^2$ in area, preferably from 1 cm$^2$ to 5 cm$^2$ and more preferably from 1 cm² to 3 cm². Several micro-needle base plates 2 may be connected to constitute a base plate of desirable size. The micro-needle base plate 2 which is 0.5 cm² or less in area is not preferable because of its inability to coat a physiologically active substance sufficiently. The micro-needle base plate 2 which is 10 cm² or more in area is not preferable either because when means for holding the base plate or the like is added, the device is excessively large in size with respect to an injection site, thus resulting in a greater size of an applicator for assisting injection.

The micro-needle 3 is a micro structure, the height (length) h of which is preferably from 50 to 550 μm. Here, the micro-needle 3 is set to be 50 μm or more in length so that a physiologically active substance is reliably injected percutaneously. And, it is set to be 550 μm or less so that any possibility that the micro-needle is in contact with a nerve is avoided to reliably decrease the possibility of pain while also reliably avoiding the possibility of bleeding. Further, the micro-needle 3 which is 550 μm or less in length is able to efficiently inject a physiologically active substance at a dosage to be injected into the skin. The micro-needle 3 is preferably from 300 to 550 μm in length and in particular, preferably from 400 to 550 μm.

Here, the micro-needle is a raised structure which means in a broad sense a needle shape or a structure including the needle shape. As a matter of course, the micro-needle shall not be limited to a needle shape having a sharp leading end but includes any shape which is not sharp at the leading end. Where the micro-needle 3 is a circular-cone structure, a base bottom thereof is about 50 to 200 μm in diameter. In the present embodiment, the micro-needle 3 is in the shape of a circular cone but may have a polygonal pyramid-shaped micro-needle such as a quadrangular pyramid. In the shape which is not sharp at the leading end, a flat part of the leading end of the micro-needle is preferably from 20 to 600 μm² in area and more preferably from 50 to 250 μm². If the flat part of the leading end is 600 μm² or more in area and where skin hardness is low, that is, where injection is performed on soft skin, the skin is completely recessed depending on the pressure of the micro-needle. Thus, a puncture has a tendency to be insufficient. On the other hand, if the flat part is 20 μm² or less in area, manufacture of the micro-needle becomes difficult and costs tend to increase although the micro-needle is able to sufficiently puncture the skin.

The micro-needles 3 are installed typically, with a space kept, so as to provide about one to ten needles in density per one millimeter (mm) of a lateral row of the needles. In general, adjacent lateral rows are separate from each other by a distance substantially equal to a space between the needles inside a lateral row, having the density of 100 to 10000 needles per cm². A needle density of 100 needles or more is able to efficiently puncture the skin. On the other hand, a needle density in excess of 10000 needles is difficult in imparting to the micro-needles 3 the strength capable of puncturing the skin. The micro-needles 3 are preferably 200 to 5000 needles in density, more preferably, 300 to 2000 needles and most preferably, 400 to 850 needles. An angle at the leading end of the micro-needle is preferably from 16 to 30 degrees, more preferably from 18 to 28 degrees and most preferably from 20 to 26 degrees.

A material of the micro-needle base plate 2 or that of the micro-needle 3 includes silicon, silicon dioxide, ceramics, metals (stainless steel, titanium, nickel, molybdenum, chrome, cobalt, etc.) and synthetic or natural resin materials, etc. When antigenicity of the micro-needle and cost of the material are taken into account, particularly preferable are synthetic or natural resin materials which are biodegradable polymers such as polylactic acid, polyglycolide, polylactic acid/co-polyglycolide, pullulan, caprolactone, polyurethane and polyanhydride as well as non-degradable polymers such as polycarbonate, polymethacrylate, ethylene vinyl acetate, polytetrafluoroethylene and polyoxyethylene, etc. Also preferable are polysaccharides such as hyaluronic acid, hyaluronate sodium, dextran, dextrin or chondroitin sulfate.

When consideration is given to a case where the micro-needle 3 is broken on the skin, it is preferable that it is made with a material of biodegradable resin and particularly preferable that it is made with polylactic acid. Polylactic acid is available as a polylactic acid homopolymer such as poly-L-lactic acid or poly-D-lactic acid, a poly-L/D-lactic acid copolymer and their mixtures, any of which may be used. Further, there is a tendency that the greater the average molecular weight of polylactic acid, the greater the strength is. It is possible to use polylactic acid with an average molecular weight of 30,000 or more.

A method for producing the micro-needle base plate 2 or the micro-needles 3 includes wet etching or dry etching using a silicon base plate and precision machining using a metal or a resin (electric discharge machining, laser machining, dicing machining, hot embossing, injection molding, etc.) and cutting using a machine. A needle portion and a supporting portion are molded integrally by these processing methods. A method for making the needle portion hollow includes a method in which secondary processing is performed by laser processing, etc., after production of the needle portion.

As shown in FIG. 2, a coating 5 is applied to the micro-needles 3 by using a coating agent which contains a physiologically active substance and a coating carrier for holding the physiologically active substance. The coating 5 is that in which the coating agent that contains the physiologically active substance and the coating carrier compatible therewith is adhered partially or entirely on the micro-needles 3 and/or the micro-needle base plate 2. "Being compatible" means that to the extent of visual assessment, no phase separation or development of aggregates is found on centrifugation operation after preparation of a solution. "Being adhered" means that there is kept a state that the coating agent is attached on a target. Immediately after coating, the coating agent is adhered in a dry state by a known drying method such as air drying, vacuum drying, freeze drying or a combination thereof. After percutaneous injection, the coating agent is not always adhered in a dry state since in some cases, moisture content held in equilibrium with a surrounding atmosphere or an organic solvent is maintained.

In FIG. 3(a) to (c), shown is one example of a method for coating the micro-needles 3. In this method, first, as shown in FIG. 3(a), a coating agent 10 is swept on the masking plate 11 by using a spatula 12 in a direction given by an arrow A, thereby filling the coating agent 10 into an opening portion 13. Then, as shown in FIG. 3(b), the micro-needles 3 is inserted into the opening portion 13 on the masking plate 11. Thereafter, as shown in FIG. 3(c), the micro-needles 3 is drawn out from the opening portion 13 on the masking plate 11. Thereby, the coating agent 10 is coated on the micro-needles 3. Thereafter, a known drying method such as air drying, vacuum drying, freeze drying or a combination thereof is used to dry the coating agent 10 on the micro-needles 3. The coating agent 10 is thereby adhered on the micro-needles 3 as the coating 5 (refer to FIG. 2 as well).

A range H of the coating of the micro-needle 3 is adjusted by a clearance (gap) C shown in FIG. 3(b). This clearance C is defined by a distance from the base bottom of the micro-needle 3 to the lower face of the masking plate 11 (the thickness of the base plate is unrelated) and set in accordance with the tension of the masking plate 11 and the length of the micro-needle 3. The distance of the clearance C is preferably in a range of 0 to 500 μm. Where the distance of the clearance C is 0, the micro-needle 3 is entirely coated. The range H of the coating which varies with the height h of the micro-needle 3 can be set to be 0 to 500 μm. The range is usually from 10 to 300 μm and preferably from about 30 to 250 μm. Where the range H of the coating is 30 μm or less, a physiologically active substance which is necessary may not be coated. Where the range is 250 μm or more, there is a tendency of availability becoming lower.

The coating 5 of the micro-needle 3 is less than 50 μm in thickness and preferably less than 25 μm and more preferably from 1 to 10 μm. In general, the thickness of the coating is an average thickness measured on the surfaces of the micro-needles 3 after drying. The thickness of the coating can be in general increased by overlaying a plurality of coating layers, that is, by further repeatedly coating the coating agent on an adhered coating layer.

In order to minimize a change in drug concentrations and a change in physical properties due to volatilization of a solvent in the coating agent on coating the micro-needle 3, it is desirable to control to constant levels temperature and humidity in an environment where the device is installed. For the purpose of preventing evaporation of the solvent, it is preferable that the temperature is lowered or the humidity is raised or both of them are controlled. Where no temperature is controlled, the humidity at room temperature is 50 to 100% RH in terms of relative humidity and preferably from 70.0 to 99.9% RH. Where the humidity is 50% RH or less, the solvent will evaporate to change the physical properties of the coating agent. Humidification can be effected by a method using air, steam or spraying water, etc. As long as intended humidity conditions can be secured, the humidification method is not particularly limited.

Physiologically active substances are drugs which exert some actions to a living body, including a low-molecular-weight compound, peptide, protein and their derivatives, etc. Physiologically active substances include high-molecular-weight compounds such as peptides, proteins, DNA and RNA. However, they are not limited in particular, and may include vaccines, low-molecular-weight peptides, sugar, nucleic acid, etc., as long as they are about 1000 in molecular weight. Physiologically active substances include, for example, α-interferon, β-interferon for disseminated sclerosis, erythropoietin, follitropin β, follitropin α, G-CSF, GM-CSF, human chorionic gonadotrophin, leutinizing hormone, salmon calcitonin, glucagon, GNRH antagonist, insulin, human growth hormone, filgrastim, heparin, low-molecular-weight heparin, somatropin, incretin, and GLP-1 derivatives, etc. Further, examples of vaccines include Japanese encephalitis vaccine, rotavirus vaccine, Alzheimer disease vaccine, arteriosclerosis vaccine, cancer vaccine, nicotine vaccine, diphtheria vaccine, tetanus vaccine, pertussis vaccine, Lyme disease vaccine, rabies vaccine, Diplococus pneumoniae vaccine, yellow fever vaccine, cholera vaccine, vaccinia vaccine, tuberculosis vaccine, rubella vaccine, measles vaccine, mumps vaccine, botulinus vaccine, herpes virus vaccine, other DNA vaccines, and hepatitis B-virus vaccine, etc.

Other examples of physiologically active substances include sleeping/sedative drugs (such as flurazepam hydrochloride, rilmazafone hydrochloride, phenobarbital and amobarbital), antipyretic, anti-inflammatory and analgesic drugs (such as butorphanol tartrate, perisoxal citrate, acetaminophen, mefenamic acid, diclofenac sodium, aspirin, alclophenac, ketoprofen, flurbiprofen, naproxen, piroxicam, pentazocin, indomethacin, glycol salicylate, aminopyrine and loxoprofen), steroid-type anti-inflammatory agents (such as hydrocortisone, prednisolone, dexamethasone and betamethasone), stimulants and analeptic drugs (such as methamphetamine hydrochloride and methylphenidate hydrochloride), psychoneurotic agents (such as imipramine hydrochloride, diazepam, sertraline hydrochloride, fluvoxamine maleate, paroxetine hydrochloride, citalopram hydrobromide, fluoxetine hydrochloride, alprazolam, haloperidol, clomipramine, amitriptyline, desipramine, amoxapine, maprotiline, mianserin, setiptiline, trazodone, lofepramine, milnacipran, duloxetine, venlafaxine, chlorpromazine hydrochloride, thioridazine, diazepam, meprobamate and etizolam), hormone drugs (such as estradiol, estriol, progesterone, norethisterone acetate, metenolone acetate and testosterone), topical anesthetic agents (such as lidocaine hydrochloride, procaine hydrochloride, tetracaine hydrochloride, dibucaine hydrochloride and propitocaine hydrochloride), drugs for urinary organs (such as oxybutynin hydrochloride, tamsulosin hydrochloride and propiverine hydrochloride), skeletal muscle relaxant agents (such as tizanidine hydrochloride, eperisone hydrochloride, pridinol mesylate and suxamethonium hydrochloride), drugs for genital organs (such as ritodrine hydrochloride and meluadrine tartrate), anti-epileptic drugs (such as sodium valproate, clonazepam and carbamazepine), autonomic nerve drugs (such as carpronium chloride, neostigmine bromide and bethanechol chloride), anti-parkinsonism agents (such as pergolide mesilate, bromocriptine mesilate, trihexyphenidyl hydrochloride, amantadine hydrochloride, ropinirole hydrochloride, talipexole hydrochloride, cabergoline, droxidopa, biperiden and selegiline hydrochloride), diuretic agents (such as hydroflumethiazide and furosemide), respiratory stimulants (such as lobeline hydrochloride, dimorpholamine and naloxone hydrochloride), anti-migraine drugs (such as dihydroergotamine mesilate, sumatriptan, ergotamine tartrate, flunarizine hydrochloride and cyproheptadine hydrochloride), anti-histamines (such as clemastine fumarate, diphenhydramine tannate, chlorpheniramine maleate, diphenylpyraline hydrochloride and promethazine), bronchodilators (such as tulobuterol hydrochloride, procaterol hydrochloride, salbutamol sulfate, clenbuterol hydrochloride, fenoterol hydrobromide, terbutaline sulfate, isoprenaline sulfate and formoterol fumarate), cardiac stimulants (such as isoprenaline hydrochloride and dopamine hydrochloride), coronary vasodilators (such as diltiazem hydrochloride, verapamil hydrochloride, isosorbide dinitrate, nitroglycerine and nicorandil), peripheral vasodilators (such as nicametate citrate and tolazoline hydrochloride), smoking cessation drugs (such as nicotine), circulatory drugs (such as flunarizine hydrochloride, nicardipine hydrochloride, nitrendipine, nisoldipine, felodipine, amlodipine besylate, nifedipine, nilvadipine, manidipine hydrochloride, benidipine hydrochloride, enalapril maleate, temocapril hydrochloride, alacepril, imidapril hydrochloride, cilazapril, lisinopril, captopril, trandolapril, perindopril erbumine, atenolol, bisoprolol fumarate, metoprolol tartrate, betaxolol hydrochloride, arotinolol hydrochloride, celiprolol hydrochloride, carvedilol, carteolol hydrochloride, bevantolol hydrochloride, valsartan, candesartan cilexetil, losartan potassium and clonidine hydrochloride), anti-arrhythmic agents (such as propranolol hydrochloride, alprenolol hydrochloride, procainamide hydrochloride, mexiletine hydrochloride, nadolol and disopyramide), anti-malignant ulcer agents (such as cyclophosphamide, fluorouracil, tegafur, procarbazine hydrochloride, ranimustine, irinotecan hydrochloride and fluridine), anti-lipemic agents (such as pravastatin, simvastatin, bezafibrate and probucol), hypoglycemic agents (such as glibenclamide, chlorpropamide, tolbutamide, glymidine sodium, glybuzole and buformine hydrochloride), peptic ulcer treating agents (such as proglumide, cetraxate hydrochloride, spizofurone, cimetidine and glycopyrronium bromide), cholagogues (such as ursodeoxycholic acid and osalmid), enterokinesis improving agents (such as domperidone and cisapride), hepatic disorder treating agents (such as tiopronin), anti-allergic agents (such as ketotifen fumarate and azelastine hydrochloride), anti-viral agents (such as acyclovir), anti-vertigenous drugs (such as betahistine mesilate and difenidol hydrochloride), antibiotics (such as cephaloridine, cefdinir, cefpodoxime proxetil, cefaclor, clarithromycin, erythromycin, methyl erythromycin, kanamycin sulfate, cycloserine, tetracycline, benzylpenicillin potassium, propicillin potassium, cloxacin sodium, ampicillin sodium, bacampicillin hydrochloride, carbenicillin sodium and chloramphenicol), agents for habitual intoxication (such as cyanamide), appetite suppressing agents (such as mazindol), chemotherapy agents (such as isoniazid, ethionamide and pyrazinamide), blood clotting promoting agents (such as ticlopidine hydrochloride and warfarin potassium), anti-Alzheimer agents (such as physostigmine, donepezil hydrochloride, tacrine, arecoline and xanomeline), serotonin receptor antagonism antiemetic agents (such as ondansetron hydrochloride, granisetron hydrochloride, ramosetron hydrochloride and azasetron hydrochloride), gout suppressants (such as colchicine, probenecid and sulfinpyrazone), and narcotic-based analgesic agents (such as fentanyl citrate, morphine sulfate, morphine hydrochloride, codeine phosphate, cocaine hydrochloride and pethidine hydrochloride).

These physiologically active substances may be used solely or in combination of two or more of them. As a matter of course, any drugs in the form of inorganic and organic salts are included in the physiologically active substances, as long as they are pharmaceutically acceptable salts. Further, a physiologically active substance is fundamentally to be contained in a coating carrier. However, a physiologically active substance is not contained in the coating carrier but can be supplied later via the through hole 4 formed on the micro-needle base plate 2.

The coating carrier includes a low-molecular-weight coating carrier and a high-molecular-weight coating carrier. The low-molecular-weight coating carrier includes proline, trehalose, sucrose, lactose, fructose, galactose, mannose, maltose, glucose, mannitol, isopropanol, propanol, butanol, propylene glycol, sorbitol and glycerin, etc. The high-molecular-weight coating carrier includes polyethylene oxide, polyhydroxymethyl cellulose, polyhydroxypropyl cellulose, polyhydroxypropylmethyl cellulose, polymethyl cellulose, dextran, polyethylene glycol, polyvinyl alcohol, polyvinyl pyrrolidone, pullulan, carmellose sodium, chondrotin sulfate, hyaluronic acid, hyaluronate sodium, dextrin and gum Arabic, etc.

Further, preferable is a coating carrier of carbohydrates which is relatively compatible (being uniformly soluble) with proteins or peptides, among physiologically active substances. More specifically, preferable are trehalose, sucrose, lactose, fructose, galactose, mannose, maltose, glucose, mannitol, polyhydroxymethyl cellulose, polyhydroxypropyl cellulose, polyhydroxypropylmethyl cellulose, polymethyl cellulose, dextran, polyethylene glycol, pullulan, carmellose sodium, chondroitin sulfate, hyaluronic acid, hyaluronate sodium, dextran, gum Arabic, etc. More preferable are polyhydroxypropyl cellulose, pullulan and gum Arabic. Particularly preferable are pullulan and sucrose. As other examples, a coating carrier which is compatible (being uniformly soluble) with proteins or peptides among physiologically active substances includes polyvinylpyrolidone, polyvinyl alcohol, carboxyvinyl polymer, polyacrylic acid, sodium polyacrylate, polyethylene oxide, polyethylene glycol, polypropylene glycol, 1,3-butylene glycol, propylene glycol, ethylene glycol and glycerin, etc.

The coating carrier is contained in the coating agent from 0.1 to 70% by weight, preferably from 0.1 to 60% by weight and in particular, preferably from 0.1 to 30% by weight. The coating carrier is required to have some extent of viscosity for preventing dripping. More specifically, the coating carrier is required to be in a range of about 100 to 100,000 cps in viscosity and more preferably in a range of 500 to 60,000 cps. The viscosity is in the above-described range, by which the coating agent can be coated all at once in a desired quantity, irrespective of a material of the micro-needle 3. Further, in general, as the viscosity becomes higher, there is a tendency for the quantity of the coating agent to increase. As a viscosity increasing agent to be mixed with the coating agent, preferably selected is pullulan which is high in humidity and moisture retaining property for suppressing volatilization of a solvent to the extent possible.

Further, to the coating agent, propylene carbonate, crotamiton, 1-menthol, peppermint, limonene, diisopropyladipate, etc., may be added, whenever necessary. As drug effect assisting agents such as a dissolution assisting agent or an absorption facilitating agent, there may be added methyl salicylate, glycol salicylate, 1-menthol, thymol, peppermint, nonylic acid vanillylamide, pepper extracts, etc to the coating agent.

Still further, a stabilizer, an antioxidant, an emulsifier, a surfactant, salts, etc., may be added to the coating agent, whenever necessary. In the present invention, the surfactant may include either a nonionic surfactant or an ionic surfactant (cation, anion or amphoteric). However, in view of safety, desirable is a nonionic surfactant which is usually used as a drug base. Included are, for example, a sugar alcohol fatty acid ester such as sucrose fatty acid ester, sorbitan fatty acid ester, glycerin fatty acid ester, polyglycerine fatty acid ester, propylene glycol fatty acid ester, polyoxyethylene sorbitan fatty acid ester, polyoxyethylene glycerin fatty acid ester, polyethylene glycol fatty acid ester, polyoxyethylene castor oil and polyoxyethylene hydrogenated castor oil.

Other known pharmaceutical auxiliary additives may be added to the coating, as long as they do not adversely influence characteristics of solubility and viscosity necessary for the coating as well as the physical integrity of the dried coating.

A liquid component used in coating the base plate 2 and/or the micro-needles 3 is prepared by mixing a volatile liquid with a biocompatible carrier, a beneficial physiologically active substance to be delivered and, when necessary, any coating assisting substances. The volatile liquid may be mixed with water, dimethylsulfoxide, dimethylformamide, ethanol, isopropyl alcohol and a mixture thereof. Among these substances, water is most preferable. A coating solution or a suspension of the liquid is typically capable of being from 0.1 to 65% by weight in beneficial drug concentration, preferably from 1 to 40% by weight and more preferably from 10 to 30% by weight in concentration. The coating is in particular, preferably in a state of being adhered. The surfactant can be available as being ambient ionic, amphoteric ionic, cationic, anionic or non-ionic. For example, it can be Tween 20, Tween 80 or other sorbitan derivatives, for example, sorbitan laurate, and alcohol subjected to alkoxylation, for example, Laureth-4. For example, addition of a surfactant is also effective in dissolving an active ingredient in a greater quantity into the coating carrier.

An injection method by using the micro-needle device 1 includes direct injection by manually pushing, an injection method by allowing the micro-needle device 1 to impact with the stratum corneum by the use of an auxiliary device such as an applicator, and an injection method by manually pushing after an auxiliary device is used, etc., however, the injection method is not limited to these methods.

There is a case that impact energy imparted by the auxiliary device to the micro-needle device 1 and the number of impacts against the micro-needle device 1 are to be changed whenever necessary, depending on the environment of the skin into which a physiologically active substance is injected. There is also a case that the auxiliary device is used to give an impact to the micro-needle device 1 several times and the device 1 is then pushed to inject the physiologically active substance.

On injection, the micro-needle device 1 which is placed on an injection site on the skin (in contact therewith) may be weighted twice or more. In other words, a load may be given to the micro-needle device 1 at least twice. Injection may be performed, for example, by manually pushing the micro-needle device 1 twice or more or by allowing the auxiliary device to work on the micro-needle device 1 twice or more. Further, when the micro-needle device 1 is weighted a plural number of times, it may be weighted in midstream by a different method. For example, it is acceptable that the auxiliary device is first allowed to work on the micro-needle device 1 once and the device 1 is then pushed manually. The micro-needle device is weighted a plural number of times, preferably two to four times and more preferably two to three times.

When an auxiliary device is used, the device applies to the micro-needle device 1 a load due to the energy of 0.05 to 0.7 J/cm$^2$, preferably a load due to the energy of 0.1 to 0.5 J/cm$^2$ and more preferably 0.2 to 0.4 J/cm$^2$. Here, the load due to the energy is a load which is produced by the energy concerned when an impact member of the auxiliary device impacts with the micro-needle device 1. When the energy is 0.05 J/cm$^2$ or less, puncture by the micro-needles is insufficient on injection into a site low in skin hardness such as the forearm, that is, into the soft skin. On the other hand, when the energy is in excess of 0.7 J/cm$^2$, pressure to the skin is excessively strong, which tends to make a patient anxious at the time of injection, and this is not desirable.

Where the micro-needle device 1 is pushed, the device 1 is pushed by the force of 1.0 to 10 kg, preferably, 1.0 to 7 kg and, more preferably, 1.0 to 4 kg. Pushing time is not long, that is, from several seconds to several minutes at the longest. The pushing time can be an instant of less than one second, depending on the situation. The pushing time is preferably within five minutes and, more preferably, within three minutes.

A method for pushing the micro-needle device 1 after the use of an auxiliary device may include a method for fixing the auxiliary device and the device 1, with the auxiliary device being placed on the device 1, thereby applying any given stress to the device 1 and a method for pushing the device 1 with fingers, etc., after medical personnel or a patient him/herself removes the auxiliary device. Further, the device 1 may be designed so that pushing stress is automatically applied inwardly (to the skin) on attachment of the micro-needle device 1 by adjusting the thickness of the micro-needle base plate 2 or the hardness of a supporting body.

As a desirable pushing method, such a method is conceivable that the micro-needle device 1 provided with a tape that has an adhesive compound is fixed on the skin, thereby injecting a physiologically active substance, with a predetermined load being applied to the device 1 (with the device 1 being in contact with the skin). For example, there is prepared a tape having an adhesive compound laminated on the supporting body, and in such a manner that an adhesive compound layer of the tape faces to the back face of the base plate 2, the micro-needle device 1 may be placed on the adhesive compound layer. Thereby, the micro-needle device 1 is fixed to a predetermined portion of the tape by adhesiveness of the adhesive compound layer, and the device 1 can be kept in contact with the skin.

The supporting body may be that which is usually used in a medical adhesive plaster, a taping agent for fixation and an adhesive skin patch. More specifically, the supporting body includes a woven fabric (including a knitted fabric) and a non-woven fabric, etc., in addition to synthetic resins such as polyethylene, polypropylene, polybutadiene, an ethylene/vinyl acetate copolymer, an acetic acid/vinyl chloride copolymer, polyvinyl chloride, polyamide, polyester, nylon, a cellulose derivative and polyurethane.

The adhesive compound is not in particular, limited as long as it is an adhesive compound which is usually used in a medical adhesive plaster, a taping agent for fixation and an adhesive skin patch. The adhesive compound includes, for example, adhesive bases, etc., which are rubber, acryl, silicone or water-soluble.

A rubber component of the rubber-based adhesive compound includes that in which one type selected from natural rubber, styrene/butadiene rubber, a styrene/isoprene/styrene block copolymer, a styrene/butadiene/styrene block copolymer, polyisoprene, polybutene, polyisobutylene and butyl rubber is used solely or two or more of them are used in combination.

The acrylic adhesive base may include any adhesive base which can be used in pharmaceutical uses. For example, it includes a high-molecular-weight acrylic adhesive compound contained in an acrylic acid/octylester acrylate copolymer, an acrylic acid 2-ethylhexyl/vinylpyrrolidone copolymer solution, an ester acrylate/vinyl acetate copolymer, an acrylic acid 2-ethylhexyl/methacrylic acid 2-etylhexyl/dodecyl methacrylate copolymer, a methyl acrylate/acrylic acid 2-ethylhexyl copolymer resin emulsion and an acryl resin alkanolamine solution.

The water-soluble adhesive base includes gelatin, pectin, agarose, alginate, xanthan gum, dextrin, methyl cellulose, ethyl cellulose, hydroxyethyl cellulose, carboxymethyl cellulose, polyvinyl alcohol, polyvinyl pyrrolidone, polyethylene glycol, a maleic anhydride copolymer, polyacrylic acid and a salt thereof or a cross linkage body or modified products of natural high-molecular-weight substances, synthetic high-molecular-weight products thereof or cross linkage products thereof, etc.

Further, in addition to the above-described adhesive compound, there may be formulated any given component used in a known adhesive compound. The above-described any given component includes, for example, an anti-oxidizing agent (such as dibutylhydroxytoluene), a softener (such as liquid paraffin, castor oil, cotton oil, palm oil, coconut oil and lanolin), an adhesiveness imparting agent (such as rosin resin, terpene resin, petroleum resin and phenol resin), an inorganic filling agent (such as zinc oxide, aluminum oxide, titanium dioxide, silica gel, magnesium oxide, ferric oxide and zinc stearate).

The micro-needle device 1 is usually placed approximately at the center of the adhesive compound layer and in contact with the skin. Therefore, the tape (the supporting body and the adhesive compound layer) is required to be greater in area than the micro-needle device 1. It is preferable that the tape is usually at least four times greater in area than the micro-needle device 1.

The adhesive compound layer and the micro-needle device 1 are covered with a liner having a raised shape until used. The liner is preferably greater in area than the tape for facilitating peeling from the adhesive compound layer. When the micro-needle device 1 is used, a user holds a portion projected from the tape with fingers to peel the liner.

With regard to a site to be injected, it is preferable that injection is performed at a site, the hardness of which is 12 or more, due to no increase in availability at a soft site, the hardness of which is 12 or less. Further, micro-needles may not be sufficient in strength at a hard site, the hardness of which is 40 or more and the site is, therefore, not desirable as a site to be injected. Here, the hardness is a value measured by using a rubber hardness tester.

EXAMPLES

Hereinafter, the present invention will be described specifically by referring to examples, however, the present invention shall not be limited to these. In the following examples, for example, a spring impact-type applicator which yields predetermined elastic energy is used as an auxiliary device. It is, however, acceptable that the applicator is not of a spring impact-type. Thus, the energy is not necessarily elastic energy.

Example 1

Where Injection by Impact was Performed Twice

A micro-needle device was used to perform in vitro injection (human skin) to determine availability. Here, the availability is a percentage of a coating agent injected into the skin with respect to the coating agent adhered on the micro-needle device.

The micro-needle device was made with polylactic acid, a base plate was 11 mm×11 mm in size, and the number of micro-needles installed on the base plate was 625 needles. Each of the micro-needles was 500 μm in height and an angle at the leading end thereof was 20 to 25 degrees. Pigment was coated on each of the micro-needles in a coating range of 150 μm in height including the top of the micro-needle concerned (that is, the range H=150 μm in FIG. 3(c)). The pigment coated on the micro-needle devices was about 23.6 μg in total, and pullulan, that is, a coating carrier, was about 58.9 μg in total.

On injection, used was a spring impact-type applicator capable of giving an impact due to the elastic energy of 0.2 or 0.3 J/cm² to the back face of the micro-needle device. It is noted that the elastic energy of the impact-type applicator can be calculated by the following formula (1).

$$1/2k(x_1^2 - x_0^2) \times 1/S \quad (1)$$

where k is a spring constant, $x_1$ is an amplitude of the spring on contraction, $x_0$ is an amplitude on impact, and S is a bottom area of the base plate of the micro-needle device. The spring constant for yielding the elastic energy of 0.2 J/cm² was 0.211 N/mm, and the spring constant for yielding the elastic energy of 0.3 J/cm² was 0.569N/mm.

The applicator was used to give an impact to the micro-needle device once or twice at the same injection position, thereby performing injection. In order to determine the availability after injection, pigment remaining on the skin after a puncture of the micro-needles was wiped off with a PBS buffer and further wiped off with a dry cloth, thereby extracting the pigment concerned. The micro-needles after peeling were submerged into the PBS buffer to extract the pigment. Then, a quantity of the pigment remaining on the skin and a quantity of the pigment remaining on the micro-needles were given as a total remaining quantity, which was divided by an initial coating quantity of the pigment to determine the availability.

Figure 4:
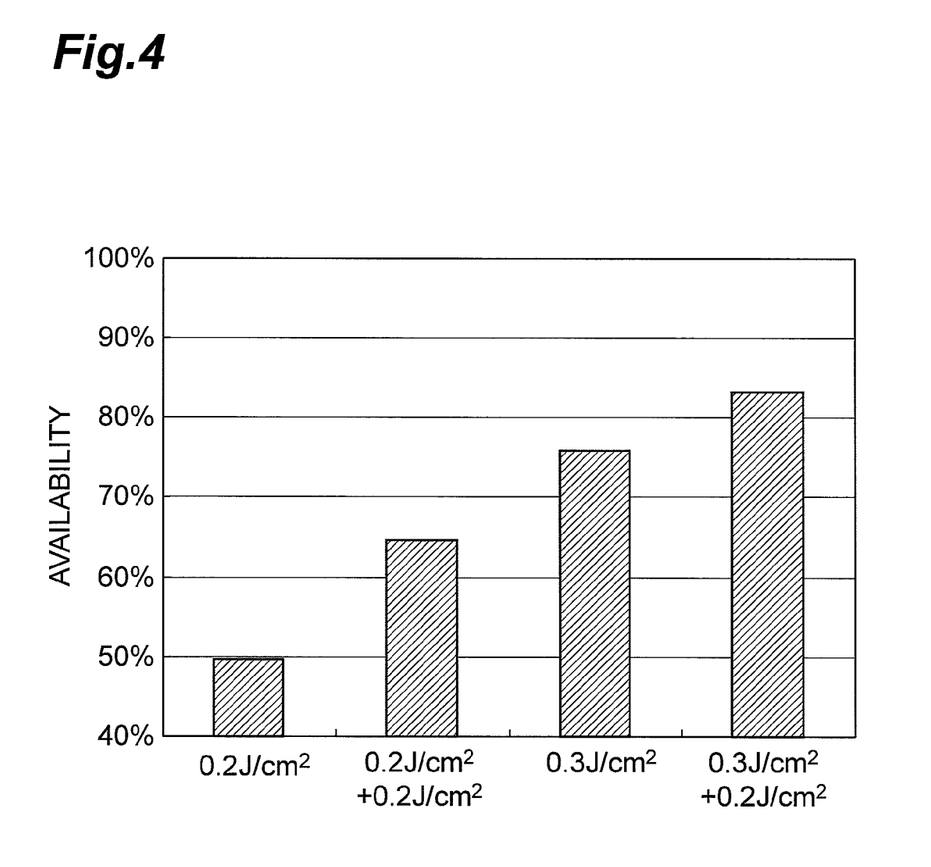
FIG. 4 is a graph which shows availability in Example 1.

The thus determined availability is shown in the graph of FIG. 4. As shown in FIG. 4, the availability determined when an impact was given once was 50% in the case of the elastic energy of 0.2 J/cm² and 75% in the case of the elastic energy of 0.3 J/cm². On the other hand, the availability determined when an impact due to the elastic energy of 0.2 J/cm² was given twice was 65%. Further, the availability determined when an impact due to the elastic energy of 0.3 J/cm² was given a first time and thereafter an impact due to the elastic energy of 0.2 J/cm² was given a second time was 82%. Therefore, it can be said that it is effective to give an impact repeatedly to the micro-needle devices (to repeatedly apply a load).

Example 2

Where Pushed After Injection by a Single Impact

Figure 3:
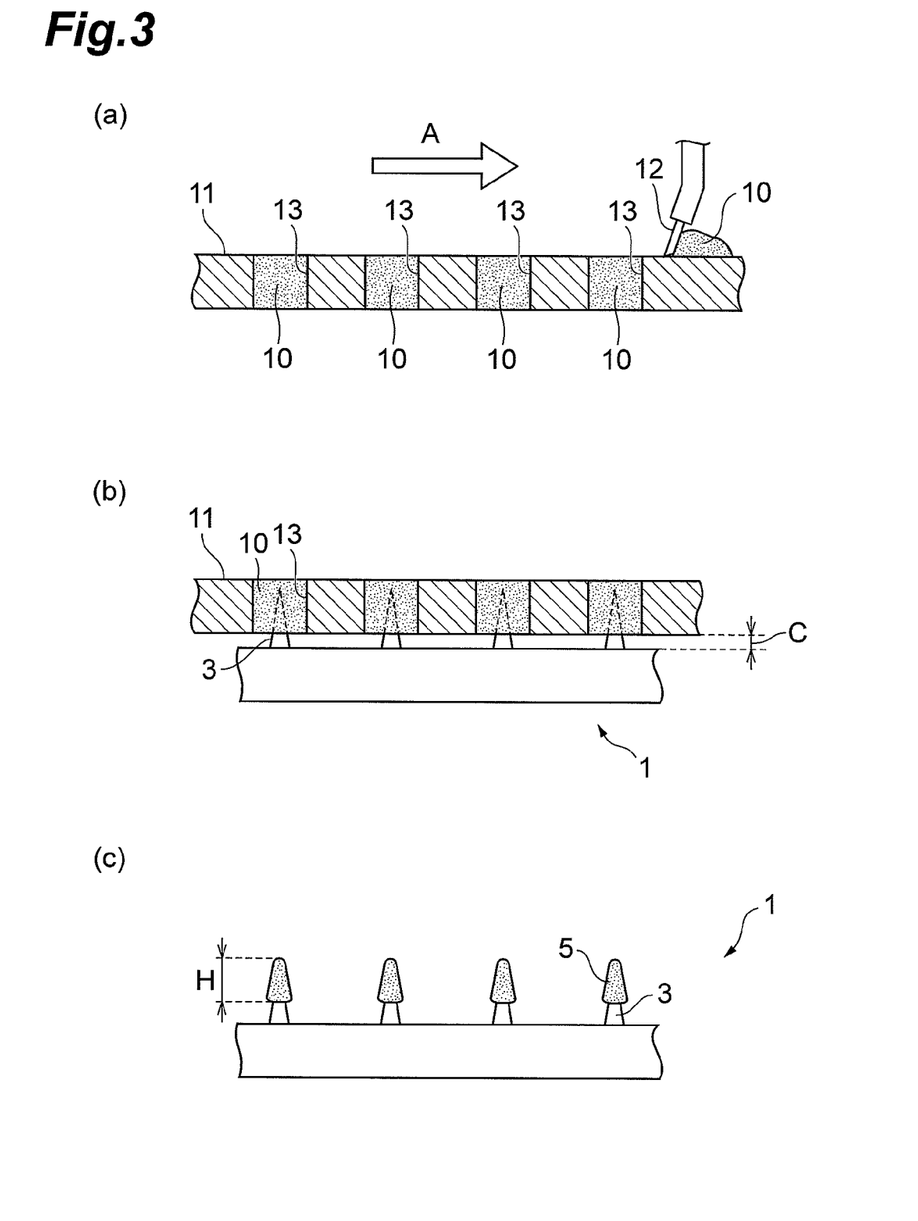

A micro-needle device similar to that of Example 1 was used to perform in vivo injection (rats) to determine availability. Here, 14C-OVA was coated on each of the micro-needles, and a coating range thereof was 200 μm in height including the top of the micro-needle concerned (that is, the range H=200 μm in FIG. 3 (c)). The 14C-OVA coated on the micro-needle device was about 100 μg in total, and pullulan, that is, a coating carrier, was about 100 μg in total.

On injection, used was a spring impact-type applicator capable of giving an impact due to the elastic energy of 0.4 J/cm² to the back face of the micro-needle device. The elastic energy of the spring impact-type applicator is determined by the above-described formula (I). A spring constant for yielding the elastic energy of 0.4 J/cm² was 0.569 N/mm. In order to determine the availability, a Geiger-Muller (GM) counter tube was used to count radiant rays, and the measurement result was applied to a previously prepared calibration curve to determine an initially coated quantity and a quantity remaining on the micro-needle device peeled after puncture. Then, the remaining quantity was divided by the initially coated quantity to determine the availability.

Figure 5:
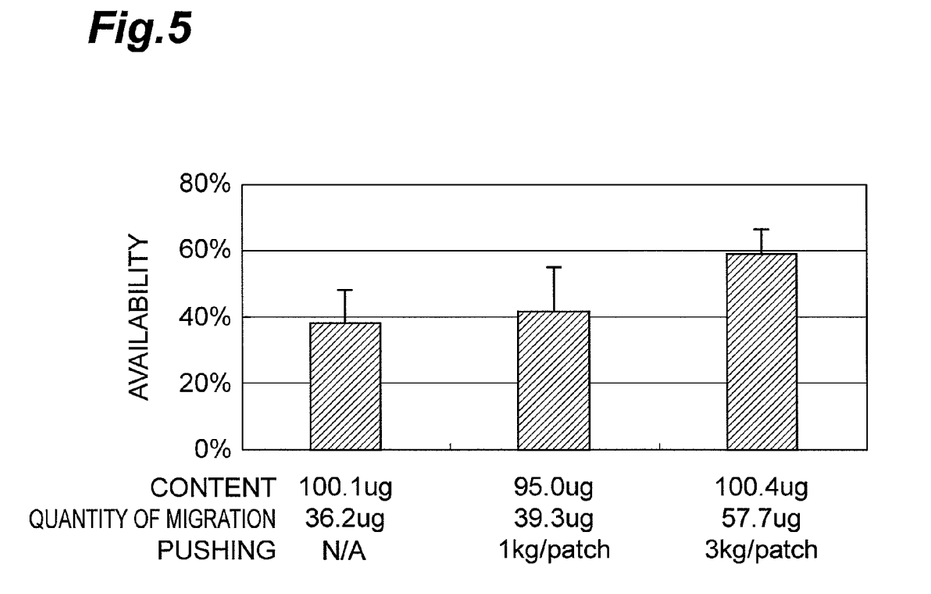
FIG. 5 is a graph which shows availability in Example 2.

The thus determined availability is shown in the graph of FIG. 5. As shown in FIG. 5, the availability determined when an impact due to the elastic energy of 0.4 J/cm² was given once was 38%. On the other hand, the availability determined when the device was pushed for one minute under stress of 1 kg/patch after an impact due to elastic energy of 0.4 J/cm² was given once was 42%. Further, the availability determined when the device was pushed for one minute under stress of 3 kg/patch after an impact due to the elastic energy of 0.4 J/cm² was given once was 58%. These results revealed that stress was applied to the micro-needle device by pushing after the use of the spring impact-type applicator, thereby increasing the availability of a drug. The results also revealed that effects of increasing the availability depended on the pushing strength.

Example 3

Comparison of Injection by Impact Given Twice with Injection by Impact Given Once and Pushing A micro-needle device similar to that of Example 1 was used to perform in vitro injection (human skin) to determine availability. Here, pigment was coated on each of the micro-needles, and a coating range thereof was 200 μm in height including the top of the micro-needle concerned (that is, the range H=200 μm in FIG. 3 (c)). The pigment coated on the micro-needles was about 72.1 μg in total and pullulan, that is, a coating carrier, was about 180.2 μg in total. On injection, used was a spring impact-type applicator capable of giving an impact due to the elastic energy of 0.2, 0.4 or 0.7 J/cm² to the back face of the micro-needle device. The elastic energy of the spring impact-type applicator is determined by the above-described formula (1). The spring constant for yielding the elastic energy of 0.2 J/cm² was 0.211 N/mm, the spring constant for yielding the elastic energy of 0.4 J/cm² was 0.569 N/mm, and a spring constant for yielding elastic energy of 0.7 J/cm² was 0.549 N/mm. The availability was determined by the same method used in Example 1.

Figure 6:
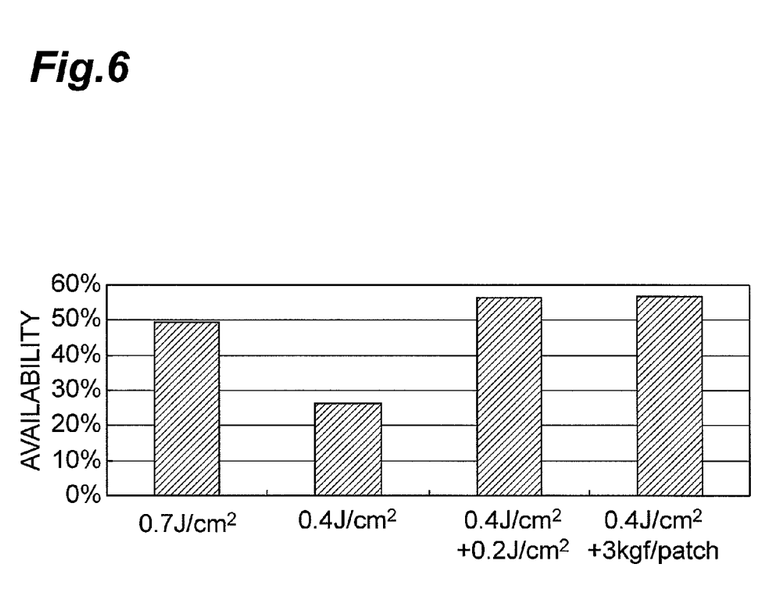
FIG. 6 is a graph which shows availability in Example 3.

The availability obtained in the present example is shown in the graph of FIG. 6. As shown in FIG. 6, the availability determined when an impact due to the elastic energy of 0.7 J/cm² was given only once was 50%, and the availability determined when an impact due to the elastic energy of 0.4 J/cm² was given only once was 25%. It can be said that these results show lower values than those obtained in Example 1 where the coating range H was equal to 150 μm. On the other hand, the availability determined when an impact due to the elastic energy of 0.4 J/cm² was given a first time and thereafter an impact due to the elastic energy of 0.2 J/cm² was given a second time was 56%. Further, the availability determined when an impact due to the elastic energy of 0.4 J/cm² was given once and thereafter the device was pushed for one minute under stress of 3 kg/patch was 57%. It can be said that the results revealed that as compared with a case where an impact due to the elastic energy of 0.7 J/cm² was given only once, a case where an impact due to weaker energy was given twice or a combined case where an impact due to weaker energy was given once and the pushing stress therewith was more likely to increase the availability of a drug.

Comparison of Example 3 with Example 1 revealed that higher availability was obtained when the coating range was 150 μm than when it was 200 μm.

Example 4

Examination of Coating Range of Micro-Needles and Energy of Applicator on Injection Into Human Skin by Micro-Needle Device A micro-needle device made with L-polylactic acid was used to perform in vitro injection (human skin: hardness of 13, 18, 23 and 32) to determine availability. Each of the micro-needles was 500 μm in height and in the shape of an approximately square pyramid, and an angle of the leading end thereof was 20 to 25 degrees. The micro-needles were 625 needles/cm² in density and a base plate was 1 cm² in area.

Pigment-containing pullulan was coated on each of the micro-needles on the micro-needle device. A coating range thereof (the range H in FIG. 3(c)) was 116, 149, 175, 208, 230 or 290 μm in height including the top of the micro-needle. The total amount of the pigment coated on the micro-needle device was 0.70 μg, 1.11 μg, 1.55 μg, 2.03 μg, 2.69 μg, and 4.37 μg, respectively, when the coating ranges were 116 μm, 149 μm, 175 μm, 208 μm, 230 μm and 290 μm.

On injection, the micro-needle device was fixed to an injection site with a tape, and an impact-type applicator was used which was capable of giving an impact due to the elastic energy of 0.2 to 0.7 J/cm² to the back face of the device. In order to determine availability after injection, the micro-needle device after peeling was submerged into a PBS buffer to extract the pigment, a quantity of which was given as a remaining quantity. Then, the remaining quantity was divided by an initial coated quantity to determine the availability.

The thus determined availability is shown in Tables 1 to 4. Parts enclosed with thick lines in the tables show that the availability was 80% or more.

TABLE 1

Human skin hardness 18

| Availability (%) | | Energy of applicator | | | | | |
|---|---|---|---|---|---|---|---|
| | | 0.1 J/cm² | 0.2 J/cm² | 0.3 J/cm² | 0.4 J/cm² | 0.5 J/cm² | 0.7 J/cm² |
| Coating height | 116 μm | 63.6% | 85.5% | 92.6% | 96.9% | | |
| | 149 μm | | 70.5% | 83.8% | 86.9% | 89.8% | |
| | 175 μm | | | 59.8% | 72.3% | 77.1% | 83.9% |
| | 208 μm | | | | | 65.5% | 74.2% |
| | 230 μm | | | | | | 55.1% |
| | 290 μm | | | | | | 26.8% |

TABLE 2

Energy of applicator: 0.2 J/cm²

| Availability (%) | | Human skin hardness | | |
|---|---|---|---|---|
| | | 13 | 18 | 23 |
| Coating height | 116 μm | 70.6% | 85.5% | 94.0% |
| | 149 μm | 62.8% | 70.5% | 83.7% |
| | 175 μm | | | 71.6% |
| | 208 μm | | | |
| | 230 μm | | | |
| | 290 μm | | | |

TABLE 3

Energy of applicator: 0.4 J/cm²

| Availability (%) | | Human skin hardness | | | |
|---|---|---|---|---|---|
| | | 13 | 18 | 23 | 32 |
| Coating height | 116 μm | 86.7% | 96.9% | | |
| | 149 μm | 80.9% | 86.9% | | |
| | 175 μm | 59.1% | 70.7% | 84.9% | |
| | 208 μm | | 54.4% | 80.1% | 94.0% |
| | 230 μm | | | 65.6% | 85.2% |
| | 290 μm | | | 44.4% | 68.8% |

TABLE 4

| | | Energy of applicator: 0.7 J/cm² | | |
|---|---|---|---|---|
| | | Human skin hardness | | |
| Availability (%) | | 13 | 18 | 23 |
| Coating height | 116 μm | 95.9% | | |
| | 149 μm | 86.2% | | |
| | 175 μm | 73.8% | 83.9% | |
| | 208 μm | 54.5% | 74.2% | 84.4% |
| | 230 μm | | 55.1% | 74.7% |
| | 290 μm | | 26.8% | 58.7% |

Tables 1 to 4 revealed that the smaller the coating range, the greater the tendency of availability. They also revealed that a physiologically active substance was able to be injected at the availability of 80% or more in various human skin hardnesses by using the micro-needle device of the present invention.

More specifically, it was revealed that the energy of the applicator which was 0.2 J/cm² or more made it possible to inject a physiological active substance at the availability of 80% or more. However, when the energy of the applicator was in excess of 0.7 J/cm², pressure to the skin was excessively strong, as describe above. Regarding a coating range (coating height), it was found that the coating range which was 230 μm or less made it possible to inject a physiologically active substance at the availability of 80% or more. However, the coating range which was less than 100 μm decreased the coating quantity itself of the physiologically active substance, resulting in a limited number of types of physiologically active substances which can be injected.

Therefore, it has been found that the coating range is adjusted from 100 to 230 μm depending on the skin hardness and also the energy of the applicator was adjusted in the range of 0.2 to 0.7 J/cm², by which a physiologically active substance can be injected at an availability as high as 80% or more.

Example 5

Examination of Skin Hardness and Availability

A micro-needle device made with L-polylactic acid was used to perform in vitro injection (human skin, dog skin and rat skin) and also in vivo injection (dogs, rats, guinea pigs, rabbits) to determine availability. Each of the micro-needles was 500 μm in height, formed in the shape of an approximately square pyramid, and a flat part of the leading end was about 100 μm² in area. The micro-needles were 625 needles/cm² in density and a base plate was 1 cm² in area.

A model peptide with a molecular weight of about 3000 was coated on each of the micro-needles on the micro-needle device. A coating range thereof (the rage H in FIG. 3($c$)) was 100 μm in height including the top of the micro-needle. The peptide coated on the micro-needle device was 82 μg in total.

On injection, used was an impact-type applicator which was capable of giving an impact due to the elastic energy of 0.4 J/cm² to the back face of the micro-needle device. In order to determine availability after injection, the peptide remaining on the skin after a puncture with the micro-needles was wiped off with a 1% aqueous solution of benzalkonium chloride and further wiped off with a dry cloth to extract the peptide. Further, the micro-needle device after peeling was submerged into the 1% aqueous solution of benzalkonium chloride to extract the peptide. Then, a quantity of the peptide remaining on the skin and a quantity of the peptide remaining on the micro-needles were given as a total remaining quantity, which was divided by an initial coating quantity to determine the availability. The hardness of each skin on in vitro or in vivo injection was measured by pushing a rubber hardness tester (manufactured by As One Corporation: WR-204A) on each skin.

Figure 7:
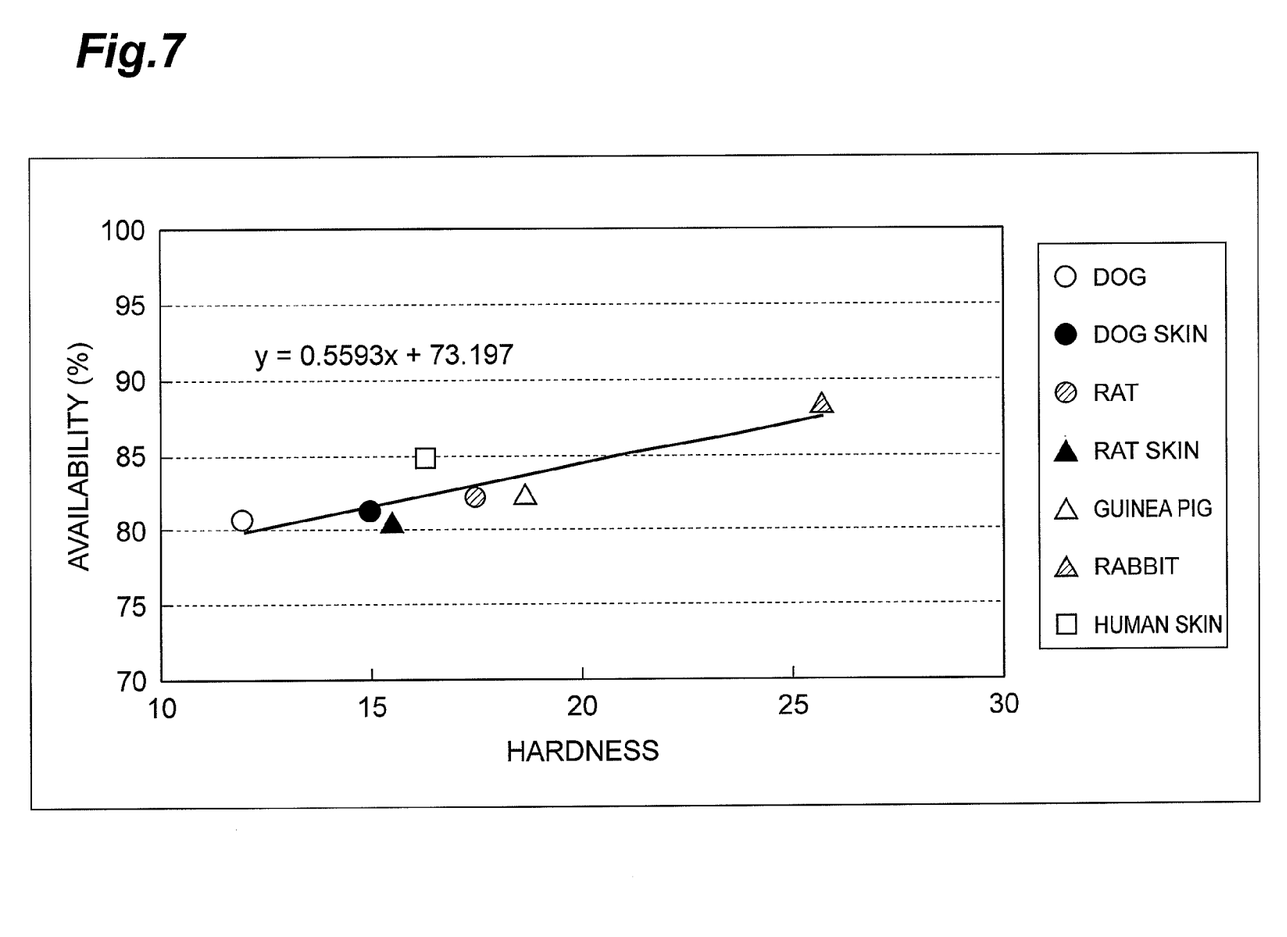
FIG. 7 is a graph which shows availability in Example 5.

The thus determined availability is shown in FIG. 7 and Table 5. When the ranges of the skin hardness were about 10 to 30, a correlation was found between the hardness x and the availability y (a relationship indicated with a direct function y=0.5593x+73.197 in FIG. 7). The higher the skin hardness, the greater the tendency of availability. Further, it was revealed that the skin hardness of 12 or more was required for securing the availability of 80% or more.

TABLE 5

| | Gel sheet | Hardness | Availability (%) |
|---|---|---|---|
| Dog | — | 12 | 80.7 |
| Dog skin | 5 | 15 | 81.2 |
| Rat | 5 | 17.5 | 82.2 |
| Rat skin | 5 | 15.5 | 80.5 |
| Guinea pig | 30 | 18.7 | 82.3 |
| Rabbit | 15 | 25.7 | 88.2 |
| Human skin | 5 | 16.3 | 84.8 |

Example 6

Skin Hardness at Each Site of Human

The skin hardness at each site of a human (inside the forearm, outside the forearm, the upper arm, above the knee region, the calf, and the abdomen) was measured by pushing a rubber hardness tester (manufactured by As One Corporation: WR-204A) on each skin. The number of subjects (n) was set to be four in each case.

TABLE 6

| Subjects (n = 4) | Average | Standard deviation |
|---|---|---|
| Forearm (inside) | 14.1 | 1.3 |
| Forearm (outside) | 21.3 | 3.6 |
| Upper arm | 23.6 | 4.1 |
| Thigh | 18.8 | 3.2 |
| Calf | 17.7 | 2.3 |
| Abdomen | 10.0 | 2.6 |

INDUSTRIAL APPLICABILITY

The present invention is able to efficiently inject a drug (physiologically active substance) and, therefore, applicable to industries.

REFERENCE SIGNS LIST

1: Micro-needle device
2: Micro-needle base plate
3: Micro-needle
4: Through hole
5: Coating
H: Coating range including the top of micro-needle

The invention claimed is:
1. A method for injecting a physiologically active substance to a patient's skin with a micro-needle device, comprising:

determining a suitable injection site on a patient in need of administration of the physiologically active substance,
preparing or obtaining a micro-needle device with micro-needles installed on a base plate, wherein
the length of the micro-needles is 300 to 550 μm,
a coating agent containing the physiologically active substance is coated at a part of the micro-needles, and
a coating range of the coating agent is 100 to 230 μm in height including the top of the micro-needles,
and injecting the physiologically active substance at the injection site by applying, at least twice, a load due to the energy of 0.2 to 0.7 $J/cm^2$ to the micro-needle device with the micro-needles in contact with the patient's skin.

* * * * *